US00PP28207P2

(12) United States Plant Patent
Jacobs

(10) Patent No.: US PP28,207 P2
(45) Date of Patent: Jul. 18, 2017

(54) ***CHRYSANTHEMUM* PLANT NAMED 'ZANMURIOT'**

(50) Latin Name: ***Chrysanthemum×morifolium* Ramat.**
Varietal Denomination: Zanmuriot

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 63 days.

(21) Appl. No.: 14/757,487

(22) Filed: Dec. 23, 2015

(51) Int. Cl.
*A01H 5/02* (2006.01)

(52) U.S. Cl.
USPC ..... Plt./289

(58) Field of Classification Search
USPC ..... Plt./289
See application file for complete search history.

*Primary Examiner* — June Hwu
(74) *Attorney, Agent, or Firm* — Steptoe & Johnson LLP

(57) ABSTRACT

A *chrysanthemum* plant named 'Zanmuriot' characterized by its medium sized blooms with yellow ray florets and prolific branching; natural season flowering date October 5; blooming for a period of 5 weeks.

3 Drawing Sheets

Botanical designation: *Chrysanthemum×morifolium* Ramat.

Cultivar denomination: 'Zanmuriot'.

RELATED CULTIVARS

This new plant cultivar 'Zanmuriot' is of the botanical classification *Chrysanthemum×morifolium* Ramat.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuriot'. 'Zanmuriot' is a product of a breeding and selection program for outdoor pot mums (garden mums) which had the objective of creating new cultivars with a double type inflorescence, a natural season flowering date around October 5, blooming for a period of 5 weeks. 'Zanmuriot' is a seedling resulting from a cross of the female parent 33114 (unpatented) with the male parent 37.9402 (unpatented). Plants of the new cultivar 'Zanmuriot' differ from plants of the female parent in the following characteristics. (1). Plant vigor—Plants of the seedling are less vigorous than those of the female parent. (2). Natural season flowering date—Plants of the seedling flower one week earlier than those of the female parents. Plants of the new cultivar 'Zanmuriot' differ from plants of the male parent in the following characteristic. (1). Plant shape—Plants of the seedling are more ball-shaped than those of the male parent.

The new and distinct cultivar was discovered and selected as a flowering plant by Henricus Cornelius Maria Jacobs on a cultivated field in Rijsenhout, The Netherlands in May 2011. The first act of asexual production of 'Zanmuriot' was accomplished in July 2011 when vegetative cuttings from the initial selection were propagated further in a controlled environment in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 20 weeks) is shown in the accompanying drawings, the color being as nearly true as possible with color photographs of this type.

DESCRIPTION OF THE INVENTION

Figure 1:
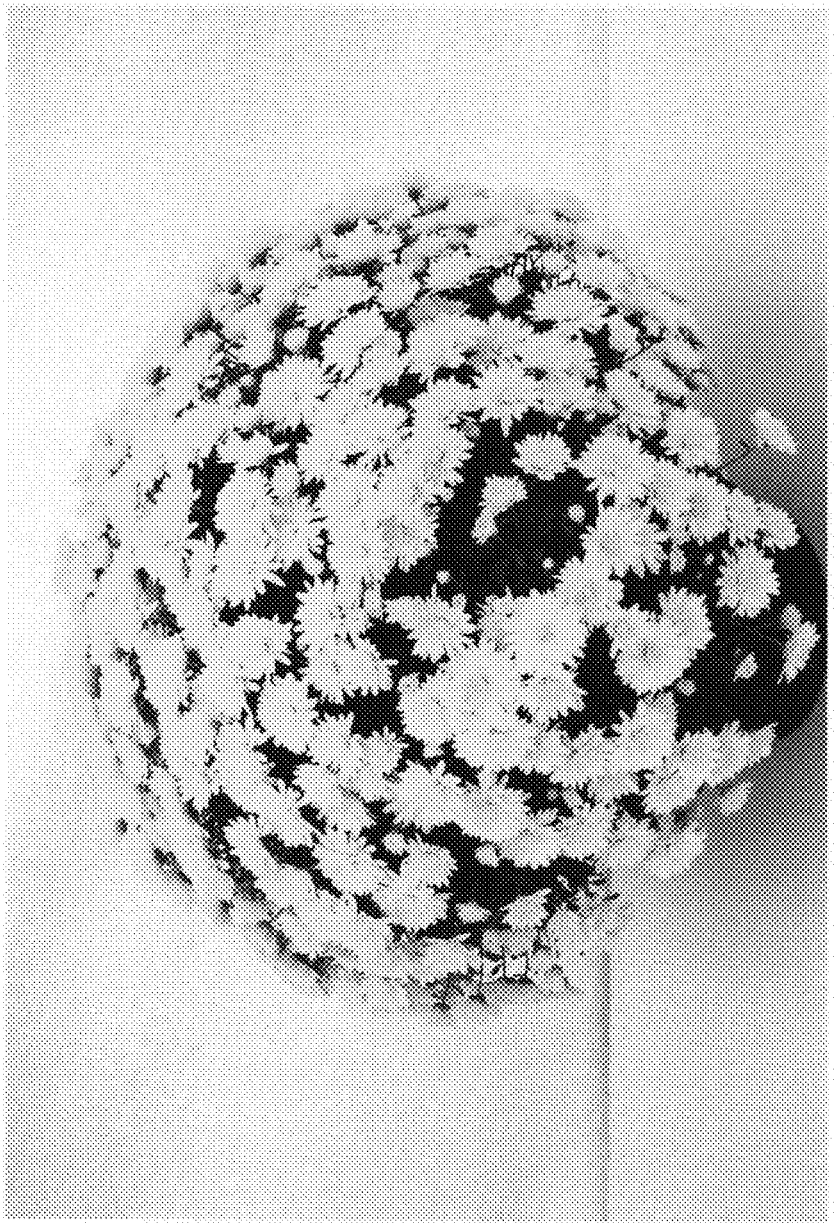
FIG. 1 shows a plant of the cultivar in full bloom.
Figure 2:
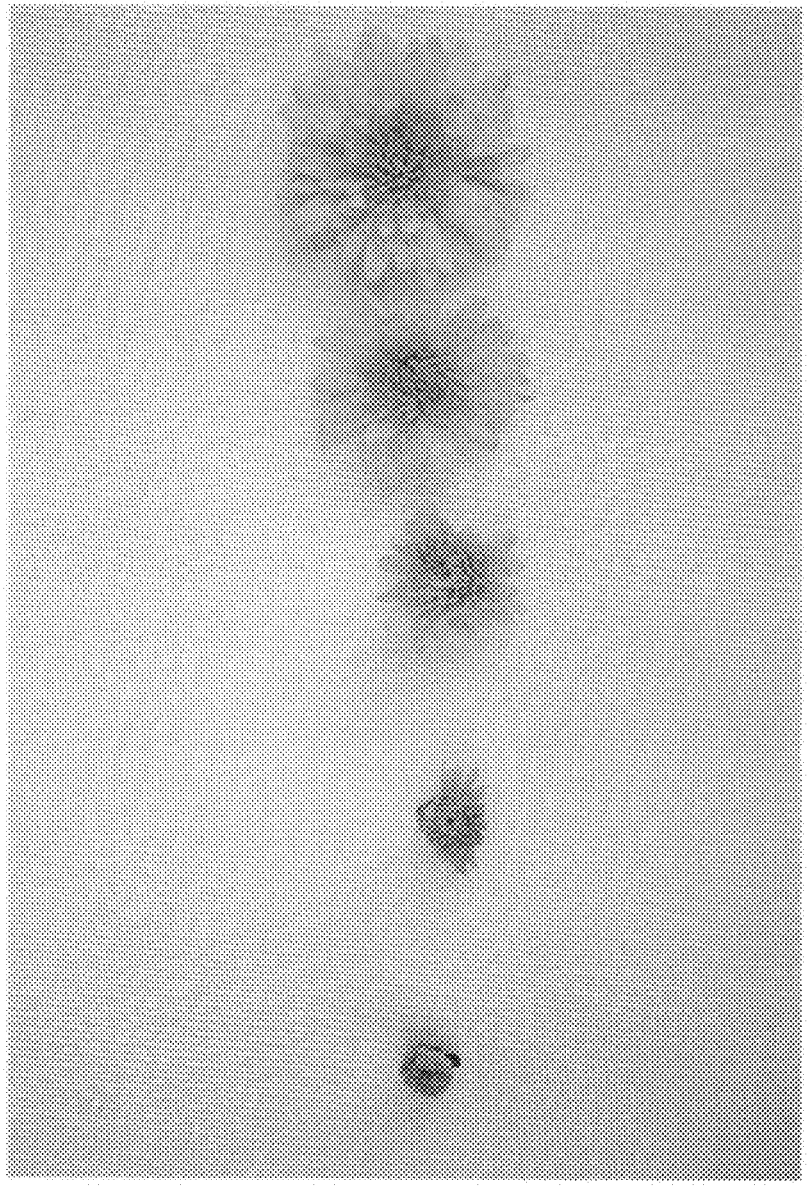
FIG. 2 shows the various stages of bloom of the new cultivar.
Figure 3:
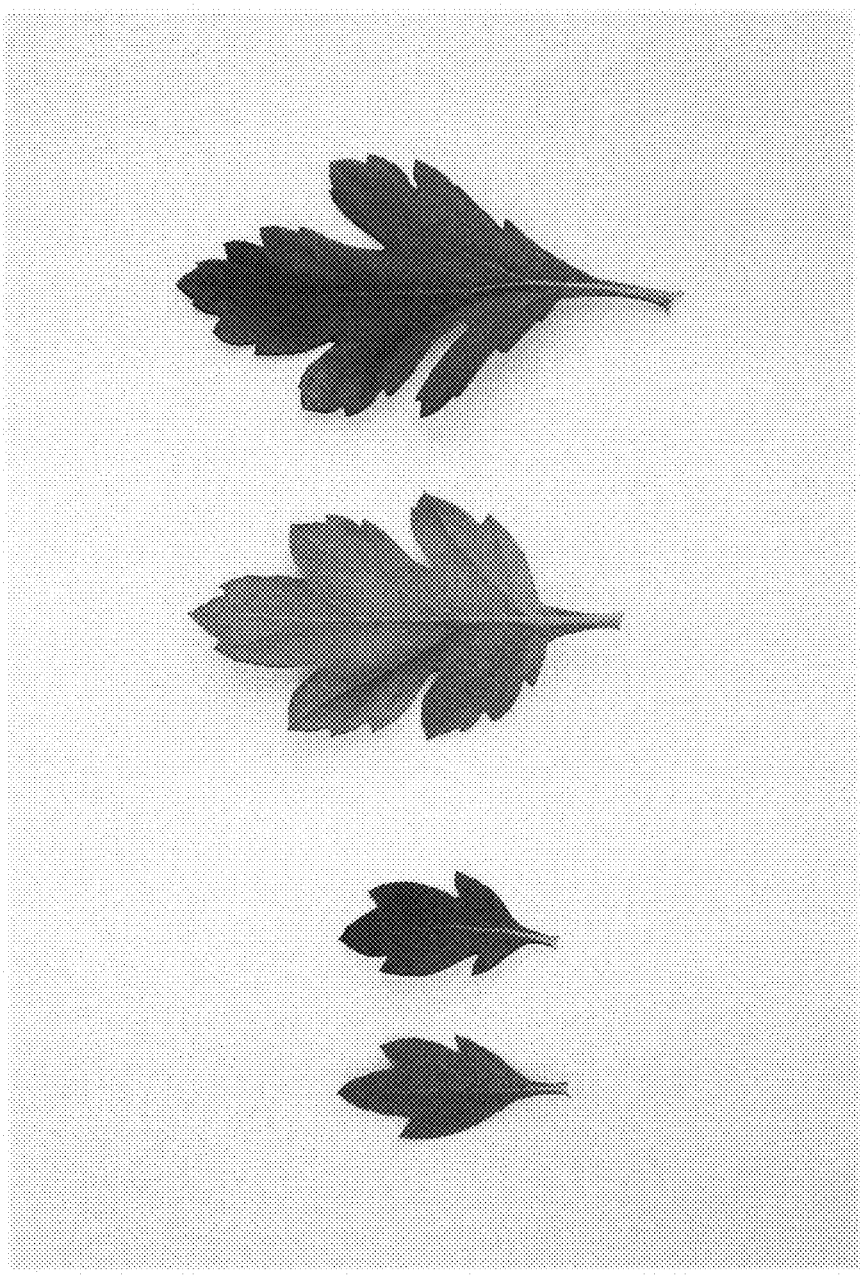
FIG. 3 shows the various stages of foliage of the new cultivar.

The observations and measurements were gathered from plants in the period of 18 to 23 weeks of age grown outdoor in Rijsenhout, the Netherlands, under natural day length and temperature and planted in week 23 in 2015, receiving drip irrigation. The natural blooming date of this crop was October 5 (week 41). The average height of the plants was 30 cm. No growth retardants were used. No tests were done on disease or insect resistance or susceptibility. No tests were done on cold or drought tolerance. This new variety produces medium sized blooms with yellow ray florets blooming for a period of 5 weeks.

From the cultivars known to the inventor the most similar existing cultivar in comparison to 'Zanmuriot' is 'Zanmusundance' (U.S. Plant Pat. No. 21,163). When 'Zanmusundance' and 'Zanmuriot' are being compared the following differences are noticed: (1). Inflorescence size. And (2). Ray-floret color. (1). Inflorescences of 'Zanmuriot' are larger than those of 'Zanmusundance'. (2). Ray-florets of 'Zanmuriot' are more deeply yellow colored than those of 'Zanmusundance'.

The following is a description of the plant and characteristics that distinguish 'Zanmuriot' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmuriot'

| | |
|---|---|
| Bud | |
| Size: | Small; cross-section 4 mm, height 3 mm |
| Shape: | Round |
| Texture: | Pubescent |
| Outside color: | Greyed-green 138B |
| Phyllaries | |
| Number: | 21-24, arranged in 3 rows |
| Shape: | Elliptic |
| Apex: | Acute |
| Base: | Truncate |
| Margin: | Entire |
| Color: | Upper side: Green 137C<br>Lower side: Green 138B |
| Length and width | 4 mm; 1 mm |
| Texture: | Pubescent |
| Inflorescences | |
| Type: | Double |
| Height: | 1 cm |
| Diameter: | 4.5 cm |
| Peduncle length: | 6-8 cm |
| Peduncle color: | Green 137B |
| Peduncle diameter: | 1 mm |
| Peduncle texture: | Pubescent |
| Number per branch: | About. 5 inflorescences |
| Duration of flowering: | 5 weeks |
| Fragrance: | Faint *chrysanthemum* odor |
| Color inflorescences | |
| Center of inflorescence: | Yellow-orange 21B |
| Color of upper side of ray florets: | Outer rows: Yellow 13A;<br>Inner Rows: Yellow-orange 21B |
| Color of lower side of ray florets: | Outer rows: Yellow 11A;<br>Inner rows: Yellow-orange 21B |
| Tonality from distance: | A garden mum with yellow blooms and a dark yellow center |
| Color of ray florets after aging of the plant: | Yellow 13A |
| Ray florets | |
| Number of types: | One |
| Type: | Ligulate |
| Texture: | Upper and lower side smooth |
| Number: | 170-180 |
| Shape: | Outer rows: Elliptic;<br>Inner rows: Narrowly elliptic |
| Apex: | Outer rows: Dentate;<br>Inner rows: Pointed |
| Base: | Attenuate |
| Cross-section: | Outer rows: Flat;<br>Inner rows: Convex |
| Longitudinal axis: | Outer rows: Straight;<br>Inner rows: Incurving |
| Length of corolla tube: | 1.5-2 mm |
| Diameter corolla tube: | 1 mm |
| Ray floret margin: | Entire |
| Ray floret length: | Outer rows: 1-2 cm |
| Ray-floret width: | Outer rows: 1.5-5 mm |
| Disc florets | Absent |
| Receptacle | |
| Color: | Yellow-green 145D |
| Shape: | Domed raised |
| Height: | 3 mm |
| Diameter: | 2 mm |
| Reproductive Organs | |
| Androecium: | Absent |
| Pollen: | Absent |
| Gynoecium: | Present on ray florets |
| Style color: | Yellow-green 154C |
| Style length: | 4 mm |

TABLE 1-continued

Botanical Description of *Chrysanthemum* × *morifolium* Ramat. 'Zanmuriot'

| | |
|---|---|
| Stigma color: | Yellow 7A |
| Stigma width: | 1 mm |
| Ovary: | Enclosed in calyx |
| Ovary color: | Yellow-green 149D |
| Seed set: | Not determined to date. |
| Plant | |
| Type: | Bushy |
| Growth habit: | Spherical shape |
| Growth rate: | Medium |
| Height: | 30 cm |
| Width: | 45 cm |
| Stem color: | Greyed-brown 199A |
| Stem strength: | Not strong |
| Stem brittleness: | Brittle |
| Stem anthocyanin coloration: | Absent |
| Internode length: | 0.3-1 cm |
| Length of lateral branch: | From top to bottom 18-20 cm |
| Lateral branch color: | Green 138B |
| Lateral branch, attachment: | Weak |
| Lateral branch diameter: | 2-3 mm |
| Lateral branch, texture: | Pubescent with ribs |
| Branching (average number of lateral branches): | Dense with 10 breaks after pinching |
| Natural season blooming date: | October 5 (week 41) in Rijsenhout, the Netherlands |
| Roots-habits: | Fine, freely branching |
| Roots-color: | White 155A |
| Foliage | |
| Glossiness: | Leaf upper side: weak<br>Leaf lower side: very weak |
| Leaf color: | Upper side: Green 137B<br>Lower side: Green 138A |
| Color midvein: | Upper side: Yellow-green 147D<br>Lower side: Yellow-green 148D |
| Size: | Small; length 4-5.5 cm, width 2-2.5 cm |
| Quantity (number per lateral branches): | 8-10 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |
| Shape of base: | Acute to truncate |
| Apex: | Mucronulate |
| Petiole strength: | Weak |
| Petiole attitude: | Moderately upwards |
| Petiole length: | 0.5-1.2 cm |
| Petiole diameter: | 2 mm |
| Petiole color: | Yellow-green 147D |
| Stipule: | Occasionally present, very small |

TABLE 2

Differences with the comparison variety, when grown under identical conditions

| | 'Zanmuriot' | 'Zanmusundance' |
|---|---|---|
| Inflorescence size | 4.5 cm | 4 cm |
| Ray-floret color | Yellow 13A | Yellow 9A |

I claim:

1. A new and distinct *chrysanthemum* plant named 'Zanmuriot' as described and illustrated.

* * * * *